US012364803B2

(12) United States Patent
Fehrenbacher

(10) Patent No.: US 12,364,803 B2
(45) Date of Patent: Jul. 22, 2025

(54) PUMP UNIT FOR MEDICAL PURPOSES

(71) Applicant: Erbe Elektromedizin GmbH, Tuebingen (DE)

(72) Inventor: Michael Fehrenbacher, Rottenburg (DE)

(73) Assignee: ERBE ELEKTROMEDIZIN GMBH, Tuebingen (DE)

( * ) Notice: Subject to any disclaimer, the term of this patent is extended or adjusted under 35 U.S.C. 154(b) by 716 days.

(21) Appl. No.: 17/527,934

(22) Filed: Nov. 16, 2021

(65) Prior Publication Data
US 2022/0168492 A1   Jun. 2, 2022

(30) Foreign Application Priority Data
Nov. 27, 2020   (EP) .................................... 20210402

(51) Int. Cl.
*A61M 1/00*   (2006.01)
*A61B 17/3203*   (2006.01)
(Continued)

(52) U.S. Cl.
CPC ........... *A61M 1/81* (2021.05); *A61B 17/3203* (2013.01); *A61M 1/743* (2021.05);
(Continued)

(58) Field of Classification Search
CPC ........ A61M 1/81; A61M 1/743; A61M 39/24; A61M 2039/267; A61M 5/16804;
(Continued)

(56) References Cited

U.S. PATENT DOCUMENTS 2,337,510 A     12/1943   Trevaskis
3,731,691 A *   5/1973   Chen ................. A61M 16/0463
                                                    604/100.01
(Continued)

FOREIGN PATENT DOCUMENTS

CN       1430524 A     7/2003
CN       1629483 A     6/2005
(Continued)

OTHER PUBLICATIONS

China National Intellectual Property Administration; Second Office Action and Search Report in corresponding Chinese Patent Application No. 202111422185.1, dated Apr. 25, 2024, 9 pages.
(Continued)

*Primary Examiner* — Jason E Flick
*Assistant Examiner* — Isabella S North
(74) *Attorney, Agent, or Firm* — Fitch, Even, Tabin & Flannery LLP

(57) ABSTRACT

A pump unit comprises at least one improved valve in which a non-ball-shaped valve closing member is reliably held in a support structure and in which the support structure is surrounded by a flow on the outside. A shank of the valve closing member is held in a pocket-shaped receptacle of the support structure such that the valve closing member is reliably held in place. The shank is located in a receptacle through which no flow passes that is formed in the support structure. The pump unit may be provided with two cylinders that are arranged in a horizontally lying manner and with one valve arranged vertically above the other. The second valve assigned to the outlet channel may be arranged directly adjacent to a cylinder wall at the vertically highest point thereof to simplify venting of the pump unit.

18 Claims, 4 Drawing Sheets

(51) Int. Cl.
*A61M 5/145* (2006.01)
*A61M 39/24* (2006.01)
*F04B 1/02* (2006.01)
*F04B 53/10* (2006.01)

(52) U.S. Cl.
CPC .......... *A61M 5/1452* (2013.01); *A61M 39/24* (2013.01); *F04B 1/02* (2013.01); *F04B 53/1087* (2013.01)

(58) Field of Classification Search
CPC .. A61M 5/16809; A61M 1/772; A61M 1/774; F04B 53/129
USPC .......................................................... 604/38
See application file for complete search history.

(56) References Cited

U.S. PATENT DOCUMENTS

| | | | | |
|---|---|---|---|---|
| 3,805,783 | A | * | 4/1974 | Ismach ................... A61M 5/30 604/71 |
| 4,054,137 | A | * | 10/1977 | Lee .......................... F04B 1/02 604/38 |
| 5,634,903 | A | | 6/1997 | Kurose et al. |
| 8,083,493 | B2 | | 12/2011 | Hagg et al. |
| 8,491,526 | B2 | | 7/2013 | Cronin et al. |
| 9,377,019 | B1 | | 6/2016 | Blume |
| 10,240,596 | B2 | * | 3/2019 | Wandel ................... F16K 21/02 |
| 2008/0069712 | A1 | * | 3/2008 | Mennicken ........... F04B 53/129 417/559 |
| 2009/0060764 | A1 | | 3/2009 | Mitzlaff et al. |
| 2009/0099478 | A1 | | 4/2009 | Cassells et al. |
| 2009/0126695 | A1 | | 5/2009 | Vu |
| 2014/0079580 | A1 | | 3/2014 | Häbe |
| 2014/0127037 | A1 | | 5/2014 | Uchida et al. |
| 2019/0011051 | A1 | | 1/2019 | Yeung |

FOREIGN PATENT DOCUMENTS

| | | | | |
|---|---|---|---|---|
| CN | 101677825 | A | | 3/2010 |
| CN | 102052292 | A | | 5/2011 |
| CN | 202971121 | U | | 6/2013 |
| CN | 103671078 | A | * | 3/2014 ......... A61B 17/3203 |
| CN | 104948446 | A | | 9/2015 |
| DE | 69429306 | T2 | | 10/2002 |
| DE | 102004031673 | A1 | | 1/2006 |
| DE | 10348832 | A1 | | 5/2006 |
| DE | 102007052755 | A1 | | 5/2009 |
| DE | 102009006042 | A1 | | 7/2010 |
| EA | 6123 | B1 | | 10/2005 |
| EP | 1839699 | A1 | | 10/2007 |
| EP | 1980291 | A1 | | 10/2008 |
| EP | 2422761 | A1 | | 2/2012 |
| EP | 2711545 | A1 | | 3/2014 |
| EP | 2758097 | A1 | | 7/2014 |
| EP | 2730240 | B1 | | 12/2014 |
| EP | 2924285 | A1 | | 9/2015 |
| EP | 1735030 | B1 | | 8/2016 |
| EP | 2222957 | B1 | | 1/2017 |
| JP | H0835574 | A | | 2/1996 |
| JP | 2009101093 | A | | 5/2009 |
| JP | 2015-187445 | A | | 10/2015 |
| JP | 2020-533533 | A | | 11/2020 |
| KR | 10-2020-0082043 | A | | 7/2020 |
| WO | 2006/088858 | A2 | | 8/2006 |
| WO | WO-2013043881 | A1 | * | 3/2013 ......... A61M 39/223 |

OTHER PUBLICATIONS

China National Intellectual Property Administration; Office Action in corresponding Chinese Patent Application No. 202111422185.1, dated Nov. 28, 2023, 13 pages.
China National Intellectual Property Administration; Search Report in corresponding Chinese Patent Application No. 202111422185.1, dated Nov. 24, 2023, 2 pages.
Extended European Search Report dated Mar. 11, 2021, in corresponding European Application No. 20210402.2, with machine English translation.
European Patent Office; European Extended Search Report in corresponding European Patent Application No. 24172399.8-1004, dated Aug. 7, 2024; 16 pages.
Federal Service for Intellectual Property of the Russian Federation; Office Action in corresponding Russian Patent Application No. 2021 133 937, dated Oct. 23, 2024; 11 pages.
Japanese Patent Office; Notice of Reasons for Refusal in corresponding Japanese Patent Application No. 2021-189357, dated Apr. 24, 2025; 12 pages.

* cited by examiner

PUMP UNIT FOR MEDICAL PURPOSES

RELATED APPLICATION(S)

This application claims the benefit of European Patent Application No. 20210402.2, filed Nov. 27, 2020, the contents of which are incorporated herein by reference as if fully rewritten herein.

TECHNICAL FIELD

The invention refers to a pump unit, particularly for medical use, e.g. for water jet surgery.

BACKGROUND

For the indicated purpose for medical or other use, piston pumps are known from DE 10 2004 031 673 A1, EP 2 730 240 B1, DE 103 48 832 A1, US 2014/0127037 A1, EP 1 735 030 B1, EP 2 222 957 B1, U.S. Pat. No. 8,491,526 B2, EP 2 758 097 A1 as well as from DE 694 29 306 T2. Such piston pumps are frequently provided with two pistons that are driven in opposite directions and alternatingly suck and convey fluid, e.g. a liquid medical treatment fluid such as, for example, sodium chloride solution. For this each cylinder is typically provided with an inlet valve and with an outlet valve that can be configured identically or differently. For this WO 2013/043881 A1 discloses a pump unit for four cylinder inlet and outlet valves in total, the valve closing members thereof are formed by a domed flexible little disc held in a valve chamber. Due to the varying fluid pressure, it opens or closes the respective inlet or outlet opening.

A pump unit having two cylinders is known from EP 2 711 545 A1, the inlet and outlet valves of which are ball valves respectively. Particularly, ball valves are used, the balls of which are loosely held in a valve chamber, i.e. they are freely movably held. The valve ball can be made of metal or plastic. The free movability of the valve balls in the valve chamber allows a particularly easy sterilization of this pump by means of sterilizing gas.

In general also valves with non-spherical and non-disc-shaped valve closing members are known, as e.g. from DE 10 2007 052 755 A1, there for hydraulic vehicle break systems. In addition, EP 1 980 291 A1 shows a valve for medical use having a substantially mushroom-shaped elastical valve closing member of rubber material. The valve closing member is located with its edge facing in shank direction on a valve seat and in this manner forms a sealing pair outside.

Also EP 2 924 285 A1 discloses a valve having a mushroom-shaped valve closing member, the edge of which comprises flow openings. Its shank projects into a downstream side flow channel, whereas its convexly curved surface facing away from the shank is seated on a valve seat. The elasticity of the substantially plate-shaped head of the valve closing member generates the spring force with which the convex sealing surface of the head abuts against a valve seat in the form of a ring rib surrounding the inlet flow channel. Such valves are in general well suitable for medical use, whereby they can reach their limits, however, in case of high flow rates. This applies particularly, if the fluid flow is so large that the valve closing member is displaced in the downstream side channel and then blocks it.

A further problem occurring with the above-mentioned pumps may result, if gas or air bubbles remain in the pump apart from the liquid to be conveyed. The pumps shall be ventable as easy as possible. In addition, the configuration is desired that is simple and can be easily maintained sterile.

It is an object of the invention to solve at least one of the above-mentioned problems.

SUMMARY

This object is solved with a pump unit as described herein.

The pump unit according to the invention comprises at least one, preferably two cylinders in which one piston is movably supported respectively. The piston is sealed against the cylinder wall and comprises for this purpose, for example, a head formed of an elastic material. At its end opposite this head a piston rod connected with the piston projects from the cylinder and is provided with a coupling device at its free end by means of which it can be coupled with a drive device preferably in a form-fit manner.

The cylinder is in connection with a first channel serving as inlet channel in which a first valve is arranged that serves as inlet valve. Also the cylinder is in connection with a second channel serving as outlet channel in which a second valve is arranged serving as outlet valve. At least one of the two valves is mushroom- or umbrella-shaped, i.e. it comprises a substantially disc-shaped head section and a shank extending away from the disc center. The valve closing member is supported in the valve with play or without play. It can be arranged in a manner to be play free supported on a valve seat with a face facing away from the shank on one side and on an abutment opposite the valve seat with a free end of the shank on the other side. Thereby the valve closing member can be made of an elastic material in one single piece, e.g. of a rubber-like material. The valve closing member can open the valve seat and thus the fluid passage in that the valve head slightly curves away from the valve seat and/or in that the shank of the valve closing member is slightly compressed. In doing so, the sealing surface of the valve closing member facing the valve seat can as a whole slightly move away from the valve seat. In this manner the flow resistance of the valve is reduced in the open position. According to this concept in which the shank of the valve closing member serves to support and center the valve closing member, it is in addition excluded that the valve closing member is carried away and forced in the downstream side channel in case of high flow velocities.

Preferably the abutment, on which the shank section is supported on its face side, is part of a support arrangement through which the fluid does not flow through and which surrounds the shank section. The face end of this support arrangement can be concurrently support surface for the head section of the valve closing member, such that it takes a defined axial position in the open position and remains reliably held. The support arrangement preferably comprises a pocket closed on five sides (on the bottom and the periphery) in which the shank section is located. The support arrangement can define a ring-shaped flow cross-section together with the channel in which it is arranged. This concept allows flow guidance with minor deflections and a reliable surrounding or support of the valve closing member. This also applies, if the valve closing member is held with play in the valve. In such embodiments it is also guaranteed that the valve closing member cannot be undesirably dislocated and in the worst case even flushed in the channel after its shank is captured in the support arrangement.

Independent from the specific configuration of the valve, it is advantageous to arrange two or more cylinders of the pump unit in use horizontally and on top of each other in a vertical direction. This simplifies venting of the pump unit.

This applies, if in each cylinder the second valve serving as outlet valve is arranged above the first valve serving as inlet valve. Thereby the outlet channel exits the cylinder close to the cylinder wall as far as possible. In doing so, air bubbles can be reliably driven out of the cylinder such that the created liquid flow precisely follows the setting by the pump.

In addition, it is advantageous in pump units according to claim 1 as well as in pump units in general, if the cylinder comprises a first section and a second section that have different diameters. Thereby the first section close to the valves preferably comprises a smaller diameter. The second section located away from the valves preferably comprises a larger diameter. The axial length of the second section is preferably at least as long as the axial length of the first section. Preferably two seals are arranged on the piston, wherein the first seal is assigned to the first section and the second seal is assigned to the second section. The distance between the first and the second seal is thereby preferably as long as the length of the first section or longer. The first seal thereby serves for sealing of the sterile pump volume that the piston limits in the cylinder. The second seal serves for sealing the pump unit to the outward and inhibits the ingress of non-sterile contaminations into the pump unit. The two seals seal at the wall of the cylinder, i.e. at its cylindrical inner surface. Bellows seals or the like can be omitted that otherwise serve for sealing of the piston rod against the cylinder.

BRIEF DESCRIPTION OF THE DRAWINGS

Further embodiments are derived from the drawings, the description or the claims. The drawings show:

DETAILED DESCRIPTION

Figure 1:
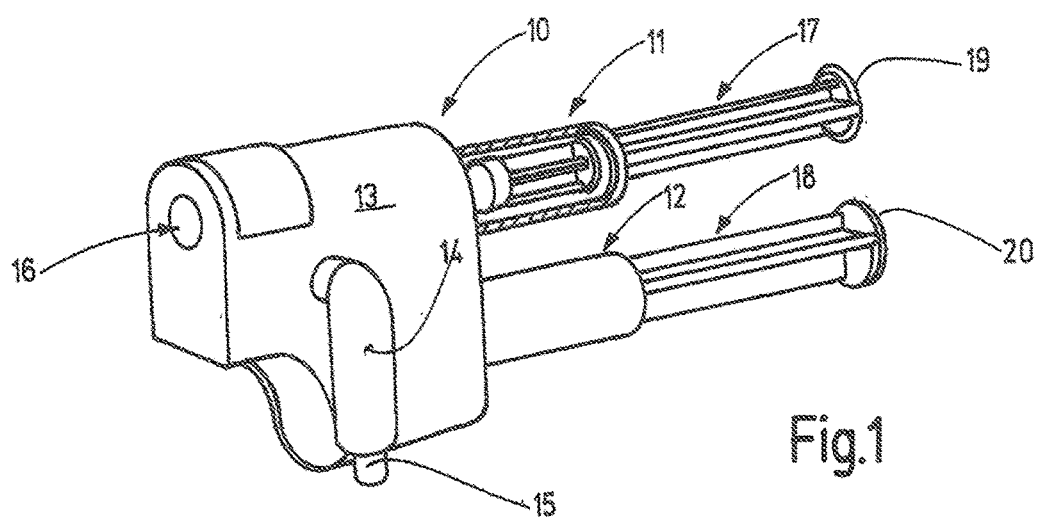
FIG. 1 a pump unit in a perspective partly cut total view.

In FIG. 1 a pump unit 10 is illustrated that can be used as sterilized medical product, e.g. in a respective receptacle of an apparatus, in order to convey a fluid, particularly a liquid. For this pump unit 10 comprises two cylinders 11, 12 as well as a cylinder head 13 from which the cylinders 11, 12 extend away. A connection piece 14 is arranged on cylinder head 13 via which fluid can be supplied to the two cylinders 11, 12 and on which a hose can be connected, e.g. on an attachment 15, leading to a liquid container, e.g. a pouch. In addition, an outlet side connector 16 is provided on the cylinder head 13 with which an instrument can be connected that has to be supplied with fluid from the pump unit 10.

Piston rods 17, 18 project from cylinders 11, 12 that are provided with coupling means 19, 20 at their free ends respectively. The coupling means 19, 20 allow the connection of piston rods 17, 18 with suitable drive devices in order to specifically axially move piston rods 17, 18 in the cylinders 11, 12, preferably opposite to one another.

The connection piece 14 mentioned above is, for example, made of flexible material and is removable from cylinder head 13. In this manner both cylinders 11, 12 can be equally supplied with fluid introduced via attachment 15. It is however also possible to connect the two cylinders 11, 12 with different fluid sources in order to output a liquid mixture or temporarily different liquids at the connector 16, e.g. flushing liquid and treatment liquid.

The two cylinders 11, 12 are preferably identically configured. The subsequent description of cylinder 11 thus also applies for cylinder 12 accordingly.

Figure 2:
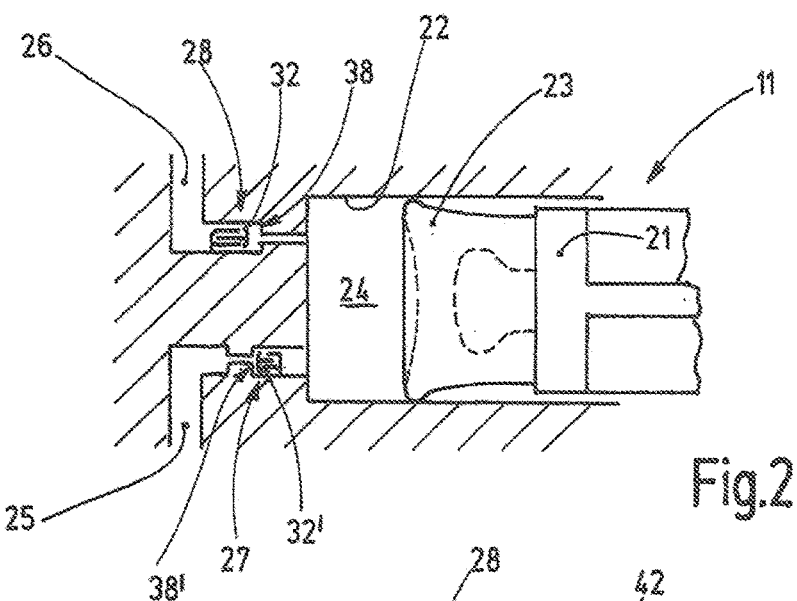
FIG. 2 a cylinder of the pump unit according to FIG. 1 with inlet and outlet channel in a longitudinal section illustration, FIG. 3 a valve of the pump unit according to FIGS. 1 and 2 in enlarged longitudinal section illustration in a closed position, FIG. 4 the valve according to FIG. 3 in open position, FIG. 5 the pump unit according to FIG. 1 in a schematic front view with accentuation of its channel extension, FIG. 6 a cylinder of pump unit according to FIGS. 1-5 in a longitudinal section illustration, FIG. 7 a pump unit similar to FIG. 2 having a modified channel arrangement and FIG. 8 a valve similar to FIGS. 3 and 4 in a modified configuration.

As illustrated in FIG. 2, a piston 21 is supported in cylinder 11 comprising a head 23 sealed against the wall 22 of cylinder 11. Head 23 together with wall 22 limits a working volume 24 inside cylinder 11 that is in connection with a first channel 25 serving as inlet channel and a second channel 26 serving as outlet channel. A first valve 27 serving as inlet valve is arranged in the first channel 25. A second valve 28 serving as outlet valve is arranged in the second channel 26.

A particularity of the inventive pump unit 10 is the configuration of at least one of the valves 27, 28. The two valves 27, 28 can be configured identically. They are self-controlled (differential pressure-controlled) valves, so-called check valves.

The following description of valve 28 applies accordingly for valve 27.

Figure 3:
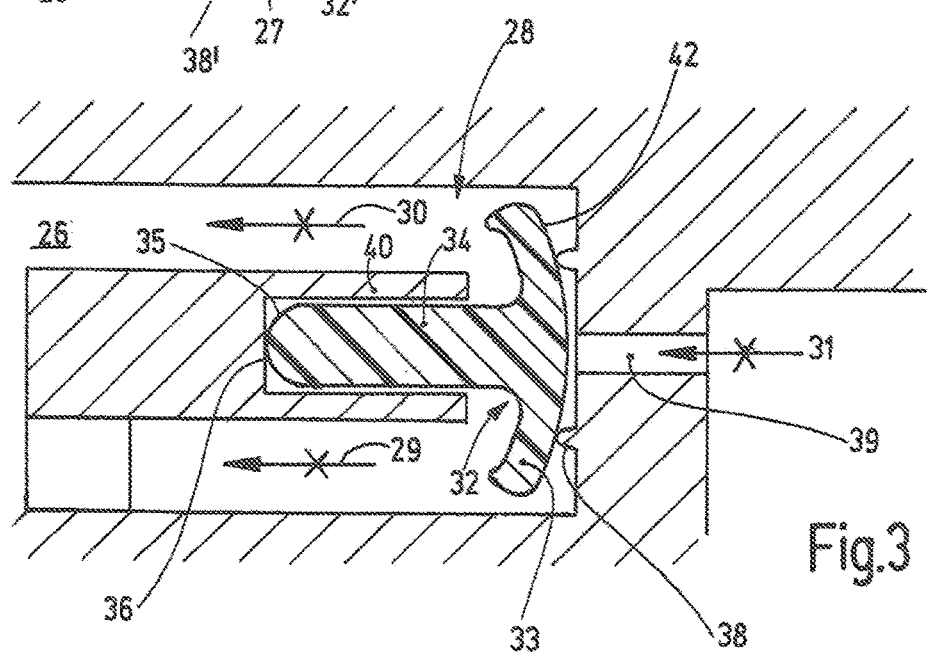

Reference is first made to FIG. 3 in which valve 28 is illustrated in rest position, i.e. closed. Arrows 29, 30, 31 indicating the flow direction are therefore illustrated in crossed manner, because no fluid flow occurs.

A valve 28 comprises a valve closing member 32 that is substantially mushroom-shaped and preferably made in one single piece of an elastic material, as apparent from the longitudinal section in FIG. 3. A preferably straight shank 34 extends away from an approximately disc-shaped, preferably slightly domed head 33. The shank 34 abuts with its distal end 35 against an abutment 36 that is immovably arranged in channel 26.

The head 33 comprises a preferably slightly domed sealing surface 42 facing away from shank 34 and abutting against a valve seat 38. The valve seat 38 is, as an example and preferably, configured as ring-shaped circular projection surrounding the inflow side part 39 of channel 26. Outside of valve seat 38 head 33 can have cavities.

The valve 28 operates as follows:

As illustrated in FIG. 3, the valve closing member 32 is held between the valve seat 38 on one side and the abutment 36 on the other side with or without play. In the embodiment according to FIGS. 3 and 4 the valve closing member 32 is held between abutment 36 and valve seat 38 without play. Channel 26 is thus blocked. Fluid does not flow in the flow direction indicated by arrows 29, 30, 31. For clarification of this circumstance, arrows 29-31 are crossed.

If now a sufficient pressure difference is created in that the piston reduces the working volume 24, the fluid present in working volume 24 urges head 33 away from valve seat 38, wherein head 33 can be slightly deformed in that its edge cambers toward the ring-shaped area of channel 26. Thereby shank 34 is reliably held in a support structure 40 immovably arranged in channel 26. Thereby abutment 36 can form the bottom of a pocket-shaped or blind hole-like cavity in which shank 34 is located and can form the end of the otherwise, for example, pin-like support structure 40 facing the head 33. The face-side end of support structure 40 facing the head 33 is preferably formed by a face 41 against which head 33 can abut, if shank 34 is compacted.

Figure 4:
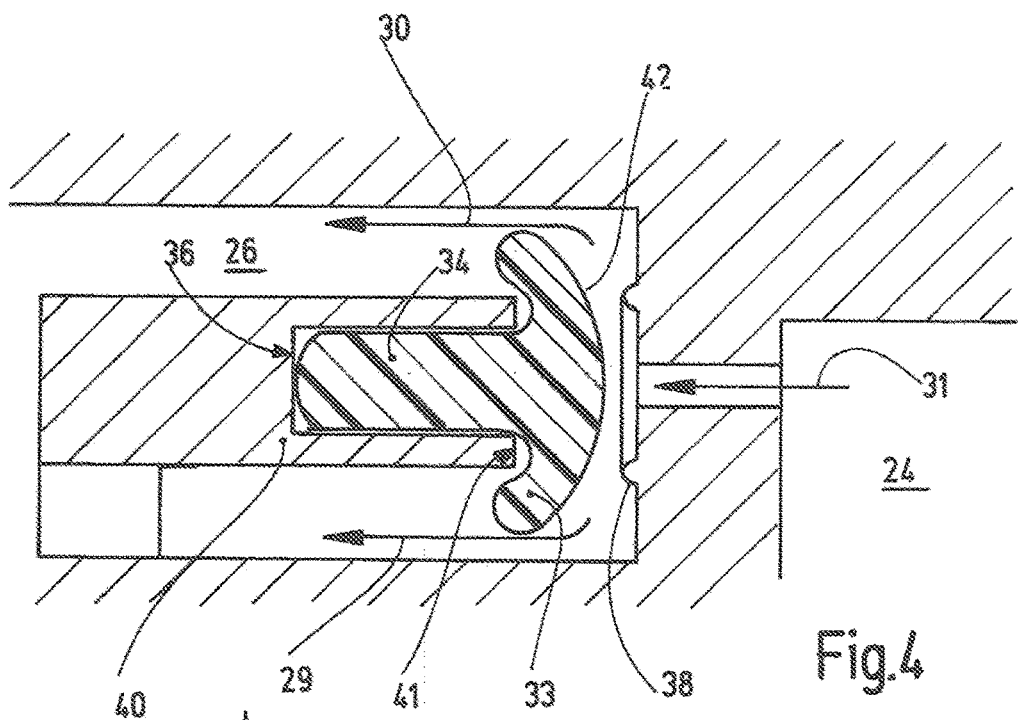

As illustrated in FIG. 4, the domed sealing surface 42 of head 33 facing valve seat 38 lifts from valve seat 38 and opens the flow path for a fluid, particularly a liquid. Thereby shank 34 can be slightly compressed and the head 33 can be slightly deformed. The arrows 29, 30 show the direction of flow passing through the ring-shaped flow cross-section of channel 26 and thus flowing around the support structure at the outside. The flow indicated by arrows 29, 30 flows from head 33 into ring cross-section of channel 26 and thereby in any case not radially inward toward shank 34.

Because shank 34 is reliably held in the support structure 40 and the fluid does not flow along shank 34, the valve closing member 32 cannot be carried away out of its receptacle into channel 26 by the flow and thus remains operable, also in case of high flow velocities. On the other hand it already reacts to slight pressure differences and thus also allows the adjustment of low effect sizes that require operation with very low flow velocities. In addition, the valve described so far is also suitable as inlet valve (valve 27 in FIG. 2). Because of the low pressure difference required for opening the valve, it is very well suitable as suction valve and is capable to suck liquid, also if cylinder 11 or 12 is first only filled with air.

Figure 5:
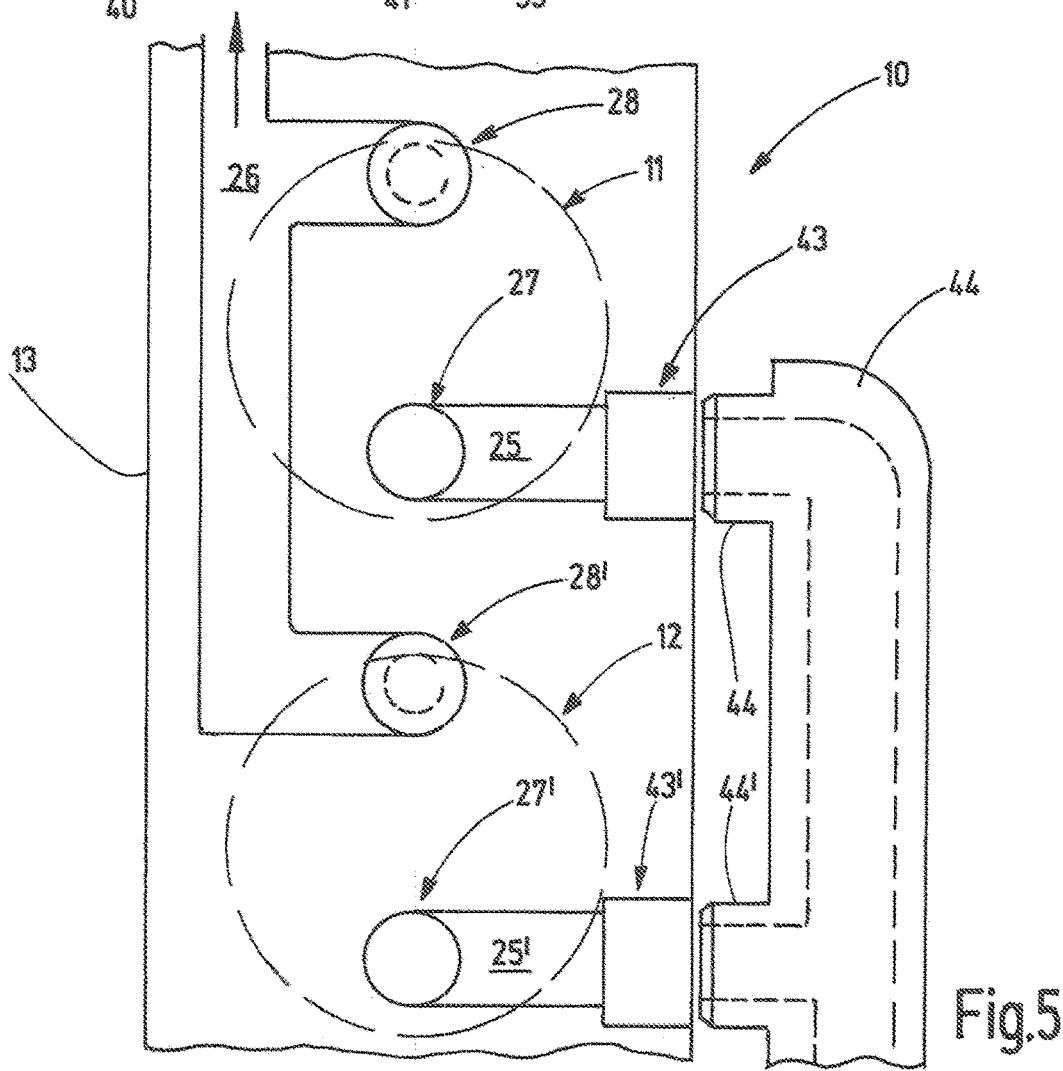
Figure 7:
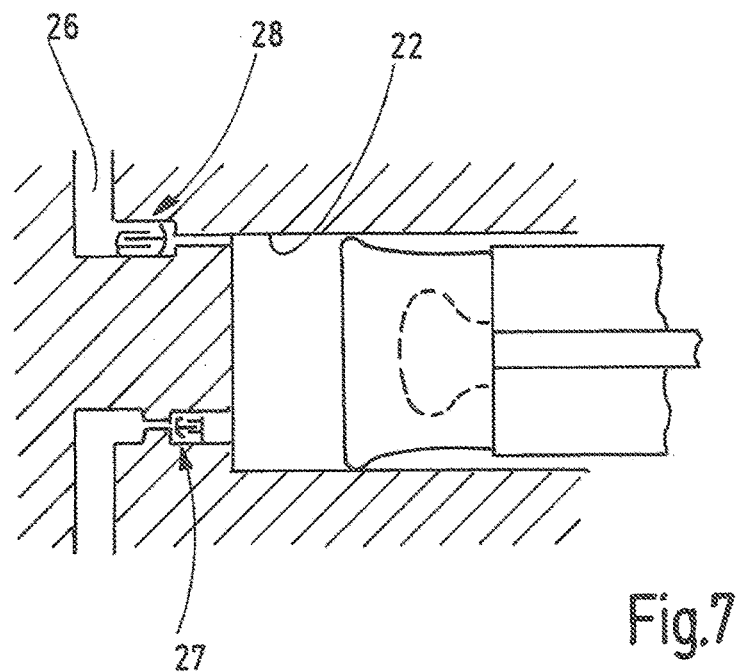

Independent from the particular configuration of valve 27 or 28, valves 27, 28 are preferably arranged on top of each other, as illustrated in FIG. 5. Thereby the upper valve 28 serves as outlet valve while the lower valve 27 preferably serves as inlet valve. Accordingly, the lower cylinder 12 comprises a first valve 27' as inlet valve and a second valve 28' as outlet valve. Thereby channel 26 is connected with both outlet valves 28, 28' that are connected with the respective cylinder 11, 12 at the top. As particularly illustrated in FIG. 7, the channel 26 preferably exits from the respective cylinder 11 or 12 in direct vicinity of wall 22. The position of first valve 27 is, however, subordinate.

According to this concept, the pump unit 10 can be particularly easily vented. Air contained in cylinders 11, 12 is easily removed by a pump movement of the respective piston and pushed out through channel 26.

While the two valves 28, 28' open out in the same channel 26 rigidly formed in cylinder head 13, the first channel 25 serving for liquid inlet can be separately accessed via a connecting structure 43, e.g. in the form of a fluid socket. This applies independent from the other configuration of the pump unit 10. The connecting structure 43 can be, for example, an opening in which a fluid plug can be inserted. Similarly first channel 25' leading to first valve 27' of second cylinder 12 can open out at a connecting structure 43', e.g. in form of a fluid socket. Thus, separate liquid containers can be connected with the two cylinders 11, 12 or channels 25, 25' respectively in order to fill the two cylinders 11, 12 with different liquids and thus to supply one and the same instrument with different liquids. It is however, also possible, as shown by FIGS. 1 and 5 together, to configure a junction piece 44, e.g. of flexible plastic, that comprises a channel that branches internally and that opens out on two plugs 44, 44' that can be inserted in the connecting structures 43, 43'.

Figure 8:
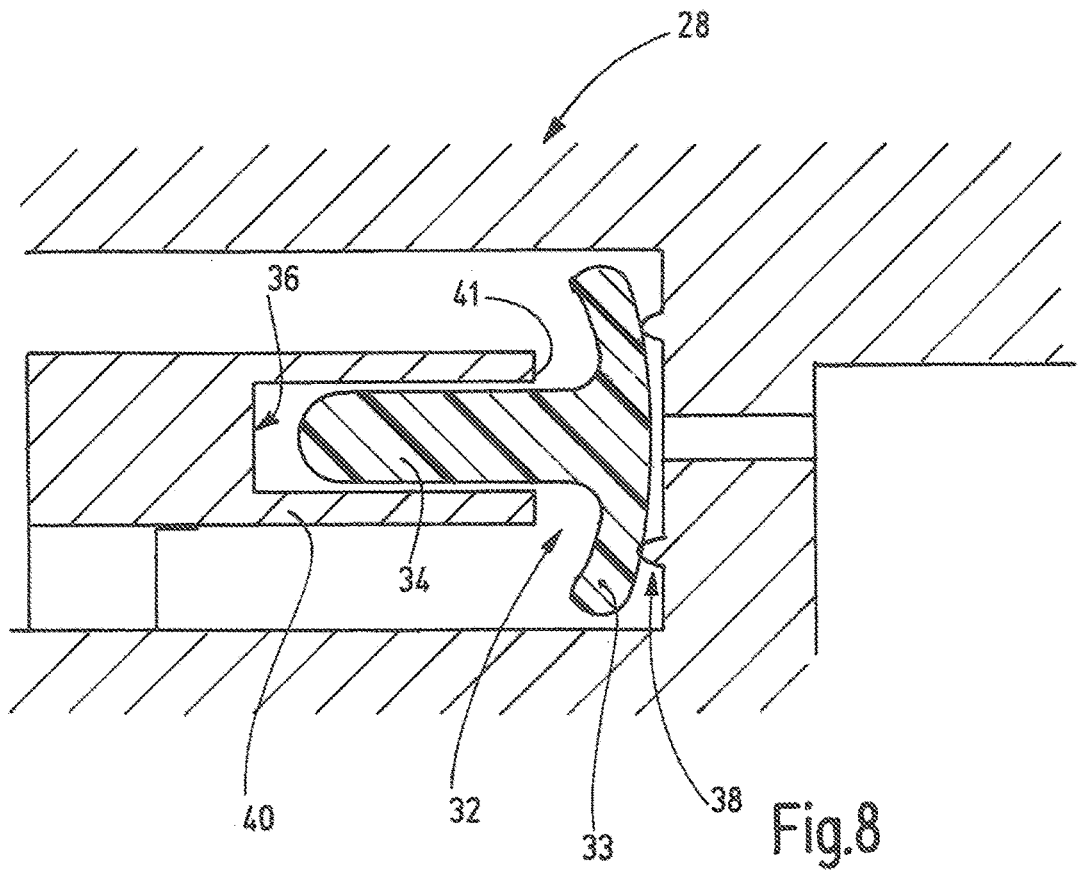

FIG. 8 illustrates a modification of valve 28 (or 27) independent from the other configuration of the pump unit 10. It can be configured as described previously or also deviate therefrom. Different to the valve 28 described above, the valve 28 illustrated in FIG. 8 comprises a support structure 40 in which the distance between abutment 36 and valve seat 38 is longer than the length of the valve closing member 32 measured in the same direction. Thus, the position of valve closing member 32 is undefined in a pressureless condition. However, slightest liquid movements are sufficient in order to abut head 33 of valve closing member 32 against valve seat 38 or to urge it away therefrom. The large umbrella-like head 33 thereby effects a reliable transition of valve closing member 32 in the closing position or open position depending on the flow direction.

Also in this embodiment of valve 28 shank 34 of valve closing member 32 is reliably held in the support structure 40 and again the face of the support structure 40 facing head 33 again forms a support surface 41 on which head 33 can be supported, if valve 28 moves in the open position. The valve 28 illustrated in FIG. 8 serves as outlet valve. In this structure it can also be also used as inlet valve. It is possible to configure both valves 27, 28 identically according to the example of FIG. 3 or 4. Both valves 27, 28 can be configured identically according to the example of FIG. 8, if desired. Furthermore, it is possible to configure a valve, e.g. the first valve 27, according to the example of FIG. 8 and the second valve 28 according to the example of FIGS. 3 and 4 or vice versa.

Figure 6:
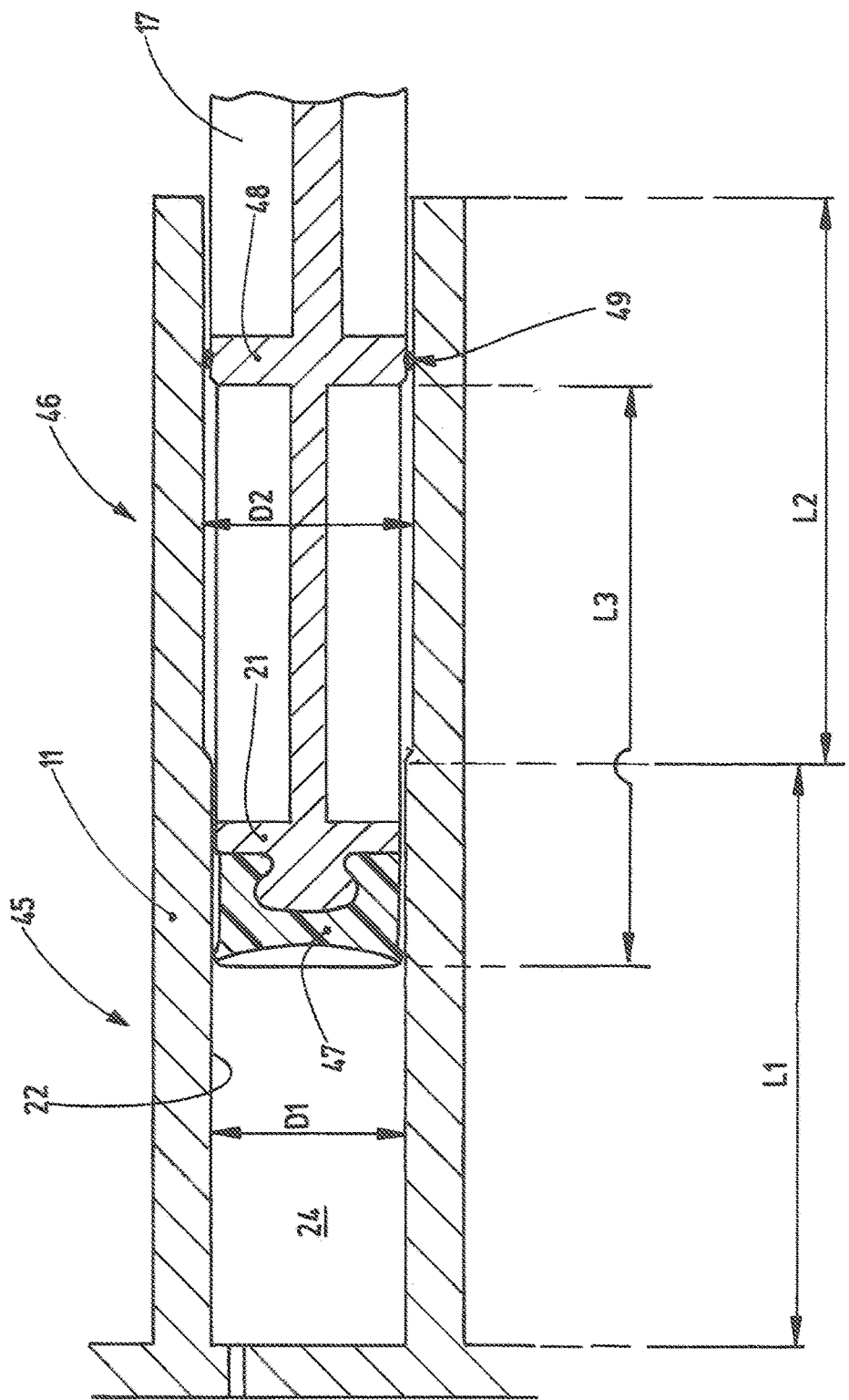

FIG. 6 illustrates the configuration of piston 21 and the assigned cylinder 11. This configuration can be selected independent from the characteristic of valves 27, 28 or other details of pump unit 10 in a pump unit having one or more cylinders. Cylinder 11 comprises a first section 45 having length L1 (pump section) in which it has a diameter D1. A second section 46 having a length L2 and a diameter D2 (sealing section) adjoins first section 45. Thereby diameter D2 is preferably at least slightly larger than diameter D1. Between both sections 45 and 46 a short conically tapering section can be provided in which wall 22 transitions from diameter D2 to diameter D1. Thereby, the length of second section L2 is preferably at least as large as length L1.

Piston 21 comprises a sealing body 47 sealing with wall 22 and comprising a rounded lip directed radially outward for this purpose. The piston 21 comprises a non-round, e.g. cross-shaped, section in an area extending away from the sealing body 47. In a distance L3 measured from the face of the sealing body 47 the piston 21 comprises a disc-shaped section 48 adjoined by piston rod 17. The disc section 48 is provided with a seal 49, e.g. an O-ring seal, a lip seal or the like, that seals with cylinder wall 22. During proper back and forth movement of piston 21, i.e. during execution of a complete pump stroke, the sealing body 47 passes through first section 45. In other words, the pump stroke of piston 21 is less than the length L1. Thus, the disc section 48 including its seal 49 moves exclusively in the second section 46. While piston 21 with sealing body 47 limits the sterile working volume 24, seal 49 of disc section 48 keeps environmental germs reliably away from the area enclosed between the sealing body 47 and the seal 49, such that the sterility of wall 22 in first section 45 can be guaranteed.

The inventive pump unit 10 comprises at least one improved valve 28 (or 27) in which a non-ball-shaped valve closing member 32 is reliably held in a support structure 40 and in which the support structure 40 is surrounded by a flow on the outside. A shank 34 of valve closing member 32 is held in a pocket-shaped receptacle of support structure 40 such that the valve closing member 32 is reliably held in place, also in case of large flow. The support structure 40 is only surrounded by a flow on the outside for this purpose. Shank 34 is located in a receptacle through which no flow passes that is formed in the support structure 40, e.g. in the form of a blind hole. Preferably the pump unit is provided with two cylinders 11, 12 that are arranged in a lying manner, thereby however vertically above each other. Particularly, however first valve 27 and second valve 28 are preferably arranged on top of each other. Preferably in turn the second valve 28 assigned to the outlet channel is arranged directly adjacent to cylinder wall 22 at the vertically highest point of cylinder wall 22. This simplifies venting of pump unit 10.

LIST OF REFERENCE SIGNS

10 pump unit
11 upper cylinder
12 lower cylinder
13 cylinder head
14 connection piece
15 attachment
16 connector
17 upper piston rod
18 lower piston rod
19 upper coupling means
20 lower coupling means
21 piston
22 wall of cylinders 11
23 head of piston 21
24 working volume
25, 25' first channel/inlet channel
26 second channel/outlet channel
27, 27' first valve/inlet valve
28, 28' second valve/outlet valve
29-31 arrows for illustrating flow direction
32 valve closing member
33 head of valve closing member 32
34 shank of valve closing member 32
35 end of valve closing member 32
36 abutment
38, 38' valve seat (rib-like ring shaped projection)
39 part of channel 26
40 support structure
41 support surface
42 sealing surface
43, 43' connection structure
44, 44' plug
45 first section of cylinder 11
L1 length of first section 45 of cylinder 11
D1 diameter of first section 45
46 second section of cylinder 11
L2 length of second section 46 of cylinder 11
D2 diameter of second section 46
47 sealing body
48 disc section
49 seal

The invention claimed is:

1. A medical pump unit (10) for supplying a medical fluid to a medical instrument, comprising:
   at least one cylinder (11, 12) with a piston (21) displaceably supported therein;
   a first channel (25) connected with the at least one cylinder (11, 12) in which a first valve (27) is arranged having a first valve closing member (32') assigned to a first valve seat (38'); and
   a second channel (26) connected with the at least one cylinder (11, 12) in which a second valve (28) is arranged having a second valve closing member (32) assigned to a second valve seat (38);
   wherein at least one of the valve closing members (32, 32') comprises an elastic shank section (34) that is disposed in a shank support structure (40), wherein the shank support structure (40) is immovably arranged in the corresponding channel (25, 26) and comprises a blind hole in which the elastic shank section (34) is disposed, wherein the shank support structure is positioned opposite from the corresponding valve seat (38, 38') and configured such that no flow can pass through the blind hole of the shank support structure (40).

2. The medical pump unit according to claim 1, wherein at least one of the valve closing members (32, 32') is seamlessly monolithically formed of an elastic material.

3. The medical pump unit according to claim 1, wherein at least one of the valve closing members (32, 32') comprises a domed sealing surface (42) facing the corresponding valve seat (38, 38').

4. The medical pump unit according to claim 1, wherein at least one of the valve seats (38) is a ring-shaped rib-like projection surrounding an inlet opening.

5. The medical pump unit according to claim 1, wherein at least one of the valve closing members (32, 32') comprises a head section (33) from which the elastic shank section (34) extends.

6. The medical pump unit according to claim 5, wherein the elastic shank section (34) has a straight and pressure-elastic configuration.

7. The medical pump unit according to claim 1, wherein another of the at least one valve closing members (32, 32') includes a shank section (34) disposed in a shank support structure (40), wherein the shank support structure is immovably arranged in the corresponding channel and at least one of the valve closing members (32, 32') is held without play between an abutment (36) formed on the corresponding shank support structure (40) and the corresponding valve seat (38).

8. The medical pump unit according to claim 7, wherein the shank support structure (40) of at least one of the valve closing members (32, 32') surrounds at least a portion of the corresponding shank section (34).

9. The medical pump unit according to claim 8, wherein the shank support structure (40) of the at least one of the valve closing members (32, 32') that surrounds at least a portion of the corresponding shank section (34) is arranged in the corresponding channel (25, 26) and defines a ring-shaped flow cross-section with a wall thereof.

10. The medical pump unit according to claim 1, further comprising two cylinders (11, 12) including the at least one cylinder (11, 12), wherein the two cylinders (11, 12) are arranged in a horizontally lying manner respectively.

11. The medical pump unit according to claim 10, wherein one of the two cylinders (11, 12) is arranged vertically above the other.

12. The medical pump unit according to claim 1, wherein the second valve (28) is arranged above the first valve (27).

13. The medical pump unit according to claim 1, wherein the at least one cylinder (11, 12) comprises a first section (45) and a second section (46), wherein the second section (46) has a diameter (D2) that is larger than a diameter (D1) of first section (45).

14. The medical pump unit according to claim 13, wherein the piston (21) is provided with a seal (47, 49) in each of the first section (45) and the second section (46) of the at least one cylinder (11, 12) that seal the piston (21) against the cylinder (11, 12).

15. The medical pump unit according to claim 14, wherein the first section (45) and the second section (46) of the at least one cylinder (11, 12) are each at least as long as a maximum pump stroke of the piston (21).

16. The medical pump unit according to claim 1, wherein the shank support structure (40) surrounds at least a portion of the elastic shank section (34).

17. The medical pump unit according to claim 16, wherein the shank support structure (40) is arranged in the corresponding channel (25, 26) in which the at least one of the valve closing members (32, 32') is arranged, and the shank support structure (40) is configured to form a ring-shaped flow cross-section with a wall thereof.

18. The medical pump unit according to claim 1, wherein a shank of the at least one valve closing member (32, 32') contacts an abutment (36) within the blind hole of the support structure (40).

* * * * *